United States Patent
Minetti et al.

(10) Patent No.: US 6,710,041 B2
(45) Date of Patent: Mar. 23, 2004

(54) PYRROLO[2,1-B][3,1] BENZOTHIAZEPINES AND THEIR USE FOR THE PREPARATION OF MEDICAMENTS WITH ANTIPSYCHOTIC ACTIVITY

(75) Inventors: Patrizia Minetti, Rome (IT); Assunta Di Cesare, Rome (IT); Domenico Mastroianni, Pomigliano d'Arco (IT); Giuseppe Campiani, Chianciano Terme (IT); Vito Nacci, Siena (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/343,627

(22) PCT Filed: Jul. 26, 2001

(86) PCT No.: PCT/IT01/00406
§ 371 (c)(1),
(2), (4) Date: Feb. 3, 2003

(87) PCT Pub. No.: WO02/10175
PCT Pub. Date: Feb. 7, 2002

(65) Prior Publication Data
US 2003/0186959 A1 Oct. 2, 2003

(51) Int. Cl.⁷ .................... C07D 513/04; A61K 31/55; A61P 25/18
(52) U.S. Cl. ................... 514/211.11; 540/547
(58) Field of Search ...................... 540/547; 514/211.11

(56) References Cited

FOREIGN PATENT DOCUMENTS
WO WO 00/06579 2/2000

OTHER PUBLICATIONS

Campiani et al, "New Antipsychotic Agents with Serotonin and Dopamine Antagonist Properties Based on a Pyrrolo[2,1–b][1,3]benzothiazepine Structure", J. Med. Chem. 41:3763–3772 (1998).

Phillips et al, "Binding of 5H–Dibenzo[b,e][1,4]diazepine and Chiral 5H–Dibenzo[a,d]cycloheptene Analogues of Clozapine to Dopamine and Serotonin Receptors", J. Med. Chem. 37:2686–2696 (1994).

Dostert et al, "Antidepressants and tricyclic neuroleptics. I. Synthesis of partially saturated analogs of the tricyclic neuroleptics clothiapine and octoclothepine", American Chemical Society 74(3):310 (1971)—Abstract.

Harris et al, "Affinity of 10–(4–Methylpiperazino)dibenz[b,f]oxepins for Clozapine and Spiroperidol Binding Sites in Rat Brain", J. Med. Chem. 25:855–858 (1982).

Jilek et al, "Nerotropic and Psychotropic Substances Further 8–Substituted 10–Piperazino–10,11–Dihydrodibenzo[b,f] Thiepins and Related Compounds. The Nor–Analogue of Octoclothepin and Its N–Substitution Derivatives", Collection of Czechoslovak Chemical Communications 36(6):2226–2247 (1971).

*Primary Examiner*—Bruck Kifle
(74) *Attorney, Agent, or Firm*—Nixon & Vanderhye P.C.

(57) ABSTRACT

A compound of formula (I):

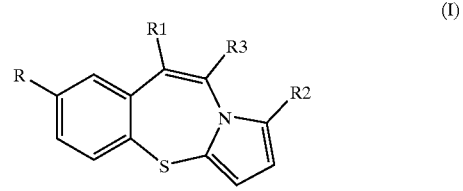

where: R=H, Cl, Br, F, I, $C_1$–$C_4$ alkoxy, $C_1$–$C_4$ alkylthio, $C_1$–$C_4$ alkyl, or $C_5$–$C_6$ cycloalkyl; $R_1$ = $C_1$–$C_4$ dialkylamine, where the alkyl groups are the same or different from one another, 4-alkyl-1-piperazinyl, 4-hydroxyalkyl-1-piperazinyl, 1-imidazolyl, 4-alkyl-1-piperidinyl, or 4-alkyl-1-homopiperazinyl; $R_2$ = H, $C_1$–$C_4$ alkoxy, $C_1$–$C_4$ alkylthio, $C_1$–$C_4$ alkyl, CHO, or CH=NOH; $R_3$ = H, CHO; or the pharmaceutically acceptable salts thereof.

14 Claims, No Drawings

PYRROLO[2,1-B][3,1] BENZOTHIAZEPINES AND THEIR USE FOR THE PREPARATION OF MEDICAMENTS WITH ANTIPSYCHOTIC ACTIVITY

The invention described herein relates to compounds for the preparation of medicaments useful for the treatment of psychiatric and neurological disorders, to processes for their preparation and to pharmaceutical compositions containing them as active ingredients. In particular, the invention described herein relates to compounds with a pyrrolobenzothiazepine structure with typical and a typical antipsychotic activity that can be formulated in pharmaceutical compositions intended for the treatment of acute and chronic psychotic states.

BACKGROUND TO THE INVENTION

The involvement of dopamine and of the dopaminergic neurons in a variety of psychiatric and neurological disorders, has now been extensively documented (E. R. Kandel, J. H. Schwartz, in "Principles of Neural Science" Neurology", Elsevier Science Publishing Co. New York, 1985).

Among the various pathologies concerned, schizophrenia is characterised by a complex symptomatology caused by abnormal neurotransmission of the main dopaminergic pathways of the central nervous system. The states of hallucination and deliria, described as positive symptoms, are due to increased activity of the mesolimbic dopaminergic pathway, while the cognitive deficits and states of social isolation, indicated as negative symptoms, are attributed to reduced dopaminergic neurotransmission in the frontal cortex.

The condition of hyperactivation of dopaminergic neurotransmission which underlies the acute and chronic psychotic states of schizophrenia, acute psychoses of unknown aetiology, and the forms of psychosis and agitation that form part of the symptomatology of other diseases, is counteracted from a therapeutic point of view by the use of classic antipsychotic agents, otherwise called neuroleptics, the most representative of which are chlorpromazine (phenothiazine class) and haloperidol (butyrophenone class).

Chlorpromazine was the first product to prove distinctly effective in the treatment of psychoses. This compound, initially used as a sedative, proved capable of improving the condition of psychotic patients, in that it was capable of inducing a particular indifference to environmental stimuli without altering the state of vigilance of the subjects using it. Thanks to the enormous commercial success of chlorpromazine, a search began in the '50s for new neuroleptic agents and this soon led to the identification of other antipsychotic products belonging to many chemical classes.

The therapeutic efficacy of the neuroleptics is related to their ability to modulate the dopaminergic neurotransmission of the central nervous system, via blockade of the dopamine receptors.

Their antipsychotic potency is directly proportional to their ability to bind and block dopamine receptors of subtype $D_2$ in the cerebral areas involved in abnormal functional dopaminergic neurotransmission. Moreover, psychopharmacology studies show that the dopaminergic hyperactivity that affects the mesolimbic pathway also involves the receptor subtypes $D_1$ and $D_3$. Consequently, the antipsychotic potency of a neuroleptic may also depend on its ability to interact with these receptors, which are densely distributed on the neuronal endings in this pathway (J. Schwartz, Giro B., M. P. Martres & P. Sokoloff "Neuroscience" 4, 99–108; 1992).

From the clinical point of view, the antipsychotic efficacy of the numerous neuroleptic agents present on the market is qualitatively equivalent in all cases. They differ only in their potency, in the sense that, whereas some of them are effective at doses of only a few mg, others need to be administered at much higher doses.

The real differences between the various neuroleptic agents depend on their ability to favour the occurrence of unwanted side effects such as arterial hypotension, sedation and, above all, severe motor abnormalities, some of which are among the most frequent manifestations associated with the clinical efficacy of the treatment. Whereas the former are due to the ability of the product to interact with the alpha-1 adrenergic and $H_1$ histaminergic receptors, respectively, the latter, common to all neuroleptic agents, are due to blockade of the $D_2$ receptors of the nigrostriatal dopaminergic system.

Pharmacological and clinical studies have shown that the simultaneous administration of neuroleptics and products with selective antagonist activity on serotoninergic $5-HT_{2a}$ receptors can increase the antipsychotic efficacy of the former and attenuate the occurrence of extrapyramidal symptoms as compared to treatment with neuroleptic agents alone (G. F. Busatto and R. W. Kerwin "Journal of Psychopharmacology" 11(1), 3–12; 1997).

Further developments in this sense have led to the generation of drugs with a mixed antagonist component, i.e. which are active on different receptors.

Clozapine (8-chloro-11-(4-methyl-1-piperazinyl)-5H-dibenzo[b,e][1,4]diazepine) is an antipsychotic agent capable of simultaneously antagonising dopamine on $D_2$ receptors and serotonin on $5-HT_2$ receptors. This new action profile, called "atypical", allows schizophrenia to be treated with a lower incidence of extrapyramidal symptoms (J. Med. Chem., 39, 1996, pp. 1172–1188).

Unfortunately, the occurrence of cases of agranulocytosis has limited the therapeutic use of this drug (Lancet. 1975, 2, 657).

Octoclothepine (8-chloro-10-(4-methylpiperazino)-10,11-dihydrodibenzo[b,f]thiepine) is a compound partly endowed with "atypical" activity. Its pharmacological activity has been studied in relation to the optical isomers of this compound (J. Med. Chem., 1991, 34, 2023–2030): a slightly greater effect on schizophrenia by the (S) form is unfortunately associated with a greater incidence of extrapyramidal effects, so that its use has been withdrawn from clinical trials. The (R) isomer presents a more "atypical" profile, with fewer side effects, but also an inferior general potency. Moreover, the two isomers prove to be endowed with the same activity as $5-HT_2$ and $D_1$ antagonists.

In view of the studies cited above, the need for antipsychotic agents with substantial therapeutic activity and without side effects remains unsatisfied. In particular, the search continues for antipsychotic agents which present greater neuroleptic activity, a lower incidence of extrapyramidal effects and minimal side effects (agranulocytosis; neutropaenia; sedation; weigh gain; costipation; urinary retention; dryness; hypotension).

ABSTRACT OF THE INVENTION

It has now been found that compounds of the 9-amino-substituted pyrrolo[2,1-b][1,3]benzothiazepine class, particularly formula (I) compounds

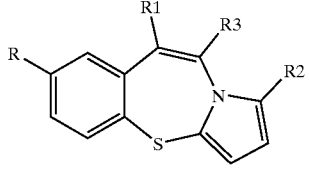

(I)

where:

R=H, Cl, Br, F, I, $C_1$–$C_4$ alkoxy, $C_1$–$C_4$ alkylthio, $C_1$–$C_4$ alkyl, $C_5$–$C_6$ cycloalkyl;

$R_1$=$C_1$–$C_4$ dialkylamine, where the alkyl groups can be the same or different from one another, 4-alkyl-1-piperazinyl, 4-hydroxyalkyl-1-piperazinyl, 1-imidazolyl, 4-alkyl-1-piperidinyl, 4-alkyl-1-homopiperazinyl;

$R_2$=H, $C_1$–$C_4$ alkoxy, $C_1$–$C_4$ alkylthio, $C_1$–$C_4$ alkyl, CHO, CH=NOH;

$R_3$=H, CHO;

are endowed with antipsychotic activity.

One object of the invention described herein therefore consists in the formula (I) compounds indicated here above and their pharmaceutically acceptable salts.

Another object of the invention described herein consists in processes for the preparation of formula (I) compounds.

A further object of the invention described herein is the use of said compounds as medicaments useful as antipsychotic agents for the treatment of psychiatric and neurological disorders, particularly disorders related to increased activity of the mesolimbic dopaminergic pathway and/or mesocortical dopaminergic hypofunction such as schizophrenia in its positive and negative symptoms.

Still another object of the present invention is the use of said compounds as medicaments, in particular as antipsychotic agents, for the treatment of psychosis, such as schizophrenia, paranoid states, manic-depressive states, affective disorders, social withdrawal, personality regression, hallucinations or cognitive dysfunctions.

Yet another object of the invention described herein consists in pharmaceutical compositions containing a formula (I) compound in a mixture with at least one pharmaceutically acceptable vehicle and/or excipient.

DETAILED DESCRIPTION OF THE INVENTION

In the formula (I) compounds, what is meant by the terms $C_1$–$C_4$ are methyl, ethyl, propyl, isopropyl, butyl, sec-butyl, and ter-butyl.

Among the formula (I) compounds, a first preferred group includes those in which $R_1$ is 4-alkyl-1-piperazinyl. A second preferred group includes those in which R is H, Cl, Br, F, I.

In particular, when R=Cl, $R_1$=4-metil-piperazin, $R_3$=H, $R_2$=H the compounds are typical antipsychotics, while for R=H,F; $R_2$=H, CHO, $CH_3$; $R_3$=H; $R_1$=4-methyl-1-piperazinyl, the compounds are a typical antipsychotics.

Among typical antipsychotics, one particularly preferred compound is 7-chloro-9-(4-methyl-1-piperazinyl)pyrrolo[2,1-b][1,3]benzothiazepine (hereinafter also referred to as ST1508), particularly the maleate (hereinafter also referred to as ST1699).

Preferred compounds of formula (I) with antipsychotic a typical activity, according to the invention are:

9-(4-methyl-1-piperazinyl) pyrrolo[2,1-b][1,3] benzothiazepine (ST1899);

7-fluoro-9-(4-methyl-1-piperazinyl)pyrrolo[2,1-b][1,3] benzothiazepine (ST1928)

1-Methyl-9-(4-methylpiperazin-1-yl)pyrrolo[2,1-b][1,3] benzothiazepine (ST2092).

The compounds according to the invention described herein are prepared starting from the formula (Ia) compound

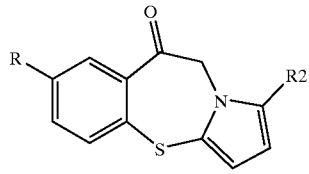

(Ia)

where R and $R_2$ are as defined above for the formula (I) compound, which is reacted with the desired amine $R_1$H as defined for the $R_1$ group to yield the formula (I) compounds.

The preparation of the formula (Ia) compound is described in patent application WO 00/06579, filed in the name of the applicant.

The transformation from compound (Ia) into compound (I) is effected with known techniques, but it has been seen that the reaction is conveniently achieved by treating compound (Ia) with amine $R_1$H in the presence of Lewis acids, e.g. triflates, such as trimethylsilyltrifluoromethane sulphonate, or protic acids, such as sulphonic acids, e.g. p-toluene sulphonic acid.

The reaction is conducted in a solvent inert to the reagents and the reaction products, or, preferably, amine $R_1$H can be used in relation to compound (Ia) in an excess such as to constitute the reaction medium. The reaction parameters are not critical and can be determined by a technician with average experience in the field on the basis of his or her own general knowledge of the subject. For example, the molar ratios of compound (Ia) to amine $R_1$H may range from 1:1 to an excess of amine in the sense referred to above. The reaction temperature will be selected also in relation to the type of reagents used, their molar ratios, and the optional presence of a solvent, in which case it may even be as high as the boiling temperature of the solvent, providing this does not lead to decomposition of the reagents themselves. The reaction times are selected on the basis of the parameters outlined above and will be such as to complete the reaction. Attempts to optimise the reaction do not constitute an additional experimental burden and are part of the normal techniques used in chemical synthesis.

The isolation and purification of the formula (I) compound are accomplished with normal known procedures.

In a first preferred embodiment of the invention, the formula (Ia) compound is reacted with amine $R_1$H, using the latter as a reaction medium, when its physicochemical characteristics so permit. The triflate preferred is trimethylsilyltrifluoromethane sulphonate. The reaction temperature is approximately 120° C. and the reaction time approximately 3 hours.

In a second preferred embodiment of the invention, the formula (Ia) compound is reacted with amine $R_1$H, using the latter as the reaction medium, when its physicochemical characteristics so permit. The preferred sulphonic acid is p-toluene sulphonic acid. The reaction temperature is approximately 180° C. and the reaction time approximately 1–2 hours.

Objects of the invention described herein are pharmaceutical compositions containing as their active ingredient at least one formula (I) compound, alone or in combination with one or more formula (I) compounds, or, said formula (I) compound or compounds in combination with other active ingredients useful in the treatment of the diseases indicated in the invention described herein, for example, other products with selective antagonist activity on the serotoninergic 5-HT$_{2a}$ receptors, also in separate dosage forms or in forms suitable for combined therapy. The active ingredient according to the invention described herein will be in a mixture with suitable vehicles and/or excipients commonly used in pharmacy, such as, for example, those described in "Remington's Pharmaceutical Sciences Handbook", latest edition. The compositions according to the invention will contain a therapeutically effective amount of the active ingredient. The doses will be determined by an expert in the field, e.g. clinician or primary care physician, according to the type of disease to be treated and the patient's condition, or concomitantly with the administration of other active ingredients. By way of an example, we may indicate doses ranging from 0.1 to 100 mg/kg.

Examples of pharmaceutical compositions are those that permit oral, parenteral, intravenous, intramuscular, subcutaneous or transdermal administration. Pharmaceutical compositions suitable for the purpose are tablets, rigid or soft capsules, powders, solutions, suspensions, syrups, and solid forms for extempore liquid preparations. Compositions for parenteral administration are, for example, all the intramuscular, intravenous and subcutaneous injectable forms, and those in the form of solutions, suspensions, and emulsions. We should also mention the forms presenting controlled release of the active ingredient, whether as oral administration forms, tablets coated with suitable layers, microencapsulated powders, complexes with cyclodextrins, depot forms, e.g. subcutaneous ones, as depot injections or implants.

The following examples further illustrate the invention.

EXAMPLE 1 a) 7-chloro-9-(4-methyl-1-piperazinyl)pyrrolo[2,1-b][1,3]benzothiazepine (10b) (ST1508)

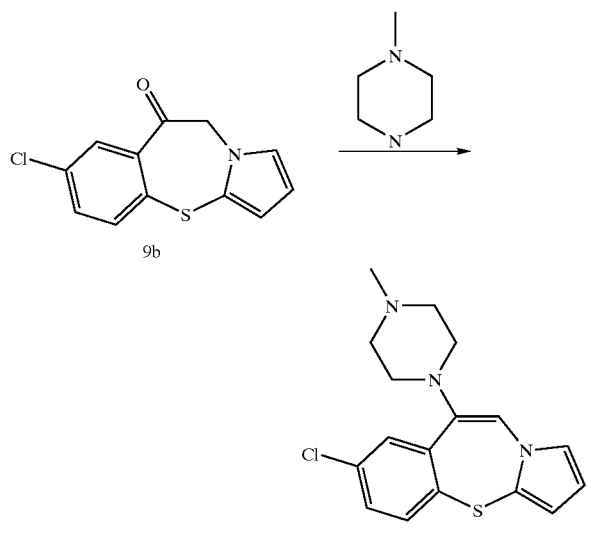

Procedure A)

To a mixture of ketone [9b] (4.5 g; 18 mmol) and N-methylpiperazine (15 ml) was added drop-wise trimethylsilyltrifluoromethane sulphonate (5.7 mL; 31.5 mmol) in 5 minutes.

The reaction temperature was brought up to 120° C. The reaction, monitored via TLC, was completed in 3 hours. The reaction mixture was left to cool at ambient temperature and the resulting solid mass was dissolved in methylene chloride (50 mL) and washed with water (2×30 mL). The organic phase was anhydrified on sodium sulphate and filtered. Evaporation of the solvent at reduced pressure enabled a crude reaction product to be recovered, which, when chromatographed on silica gel (n-hexane/ethyl acetate 50:50) finally yielded 4.7 g of the title compound.

Yield: 78%

TLC (AcOEt) Rf=0.25; MP: 127÷128° C.

$^{1}$H-NMR (300 MHz, CDCl$_3$) δ 7.6 (d, 1H, J=2.1 Hz); 7.4 (d, 1H, J=8.5 Hz); 7.2 (dd, 1H, J$_1$=8.4 Hz, J$_2$=2.0 Hz); 6.7 (m, 1H); 6.6 (m, 1H); 6.2 (m, 1H); 6.1 (m, 1H); 2.9 (m, 4H); 2.6 (m, 4H); 2.3 (s, 3H).

$^{13}$C-NMR (300 MHz CDCl$_3$) δ 143.8; 140.5; 137.9; 134.8; 133.2; 129.8; 129.6; 127.9; 123.2; 112.7; 111.6; 111.2; 55.2; 50.1; 46.2.

Elemental analysis: (C$_{17}$H$_{18}$ClN$_3$S): compliant.

Procedure B)

A mixture of ketone [9b] (0.15 g; 0.6 mmol), N-methylpiperazine (0.18 g; 1.8 mmol) and p-toluene sulphonic acid (0.296 g; 1.56 mmol) was heated to 180° C.

The reaction, which rapidly took on a dark colouring, was completed in 1.5 hours. After cooling at ambient temperature, the resulting solid mass was dissolved in methylene chloride (10 mL) and washed with water (2×10 mL). The organic phase was anhydrified on sodium sulphate and filtered. Evaporation of the solvent at reduced pressure yielded a crude reaction product which, when chromatographed on silica gel (n-hexane/ethyl acetate 50:50), yielded 0.10 g of the title compound.

Yield: 50%

EXAMPLES 2–13

The synthesis of products 2–13 has been carried out following approaches described in schemes 1

1-11

|    | R  | R$^1$ | R$^2$    | R$^3$ | n | ST   |
|----|----|-------|----------|-------|---|------|
| 2  | H  | Me    | H        | H     | 1 | 1899 |
| 3  | H  | Me    | CHO      | H     | 1 | 2091 |
| 4  | H  | Me    | CHO      | CHO   | 1 | 2147 |
| 5  | H  | Me    | Me       | H     | 1 | 2092 |
| 6  | H  | Me    | CH=NOH   | H     | 1 | 2129 |
| 7  | H  | Me    | CH$_2$OH | H     | 1 | 2096 |
| 8  | H  | Me    | CH$_2$O/Pr | H   | 1 | 2095 |
| 9  | Cl | Et    | H        | H     | 1 | 2148 |
| 10 | Cl | Me    | H        | H     | 2 | 2149 |
| 11 | Br | Me    | H        | H     | 1 | 2093 |
| 12 | Br | Et    | H        | H     | 1 | 2150 |
| 13 | F  | Me    | H        | H     | 1 | 1928 |

R$^1$ in the above table identifies the 4-alkyl substituent on the piperazine ring.

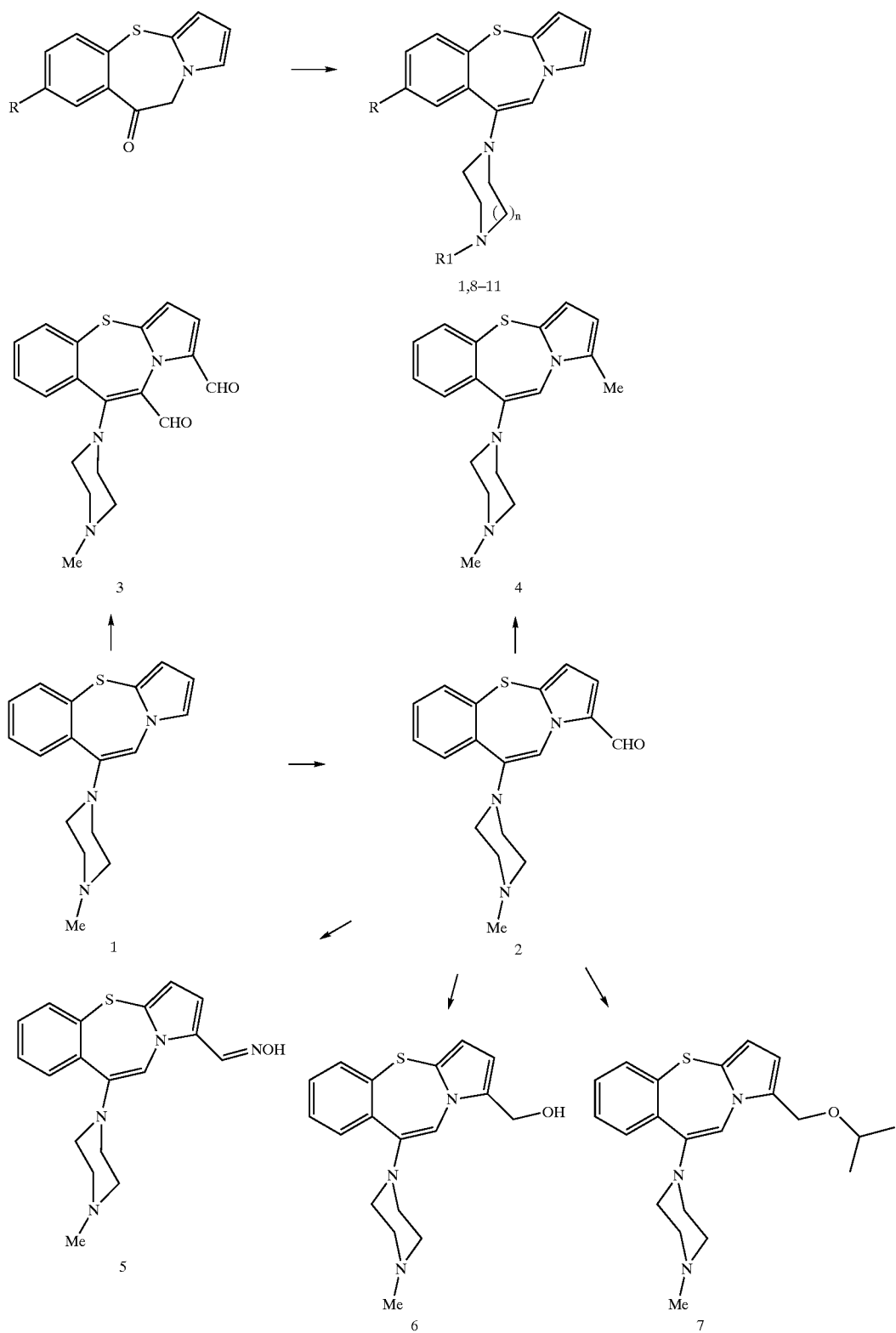

9-(4-Methylpiperazin-1-yl) Pyrolo [2,1-b][1,3] benzothiazepine (1) (ST1899)

A solution of 9,10-dihydropyrrolo[2,1-b][1,3] benzothiazepin-9-one (0.24 g, 1.11 mmol), N-methylpiperazine (0.55 mL, 0.50 g, 4.99 mmol) and trimethylsilyl triflate (0.55 mL, 0.68 g, 3.05 mmol) was heated at 120° C. under stirring, after a few minutes further 0.55 mL of N-methylpiperazine were added and the reaction was kept for 3 hours at 120° C. After that time water was added and was extracted with dichloromethane. The organic layer was dried over sodium sulphate, filtered and evaporated to give the crude product that was purified by means of a flash chromatography (20% methanol in ethyl acetate) to afford 0.114 g of the pure title compound as a yellowish solid (84% yield).

$^1$H NMR (CDCl$_3$) δ 7.65 (m, 1H), 7.50 (m, 1H), 7.34–7.22 (m 2H), 6.75 (m, 1H), 6.20 (m, 1H), 6.12 (m, 1H), 2.89 (m, 4H), 2.53 (m, 4H), 2.34 (s, 3H).

Elemental analysis (C$_{17}$H$_{19}$N$_3$S): compliant.

9-(4-Methylpiperazin-1-yl)pyrrolo[2,1-b][1,3]benzothiazepine-1-carbaldehyde (2) (ST2091)

A mixture of phosphorus oxychloride (50.70 μL, 0.08 g, 0.54 mmol) and N-methylformanilide (67.15 μL, 0.07 g, 0.54 mmol) was stirred for 30 minutes at room temperature. Then solid (1) (0.12 g, 0.42 mmol) was added and the resulting mixture was stirred overnight at room temperature. Then water was added and the water phase was extracted with dichloromethane (3×2.5 mL). Combined organic layers were dried over sodium sulphate, filtered and evaporated. Purification was accomplished by means of flash chromatography (5% methanol in dichloromethane) and afforded 0.05 g of the pure desired product as a yellowish crystalline solid (37% yield).

$^1$H NMR (CDCl$_3$) δ 9.45 (s, 1H), 7.65 (m, 1H), 7.46 (m, 1H), 7.32 (m, 2H), 7.04 (s, 1H), 6.93 (d, 1H, J=3.9 Hz), 6.24 (d, 1H, J=4.3 Hz), 3.15–2.95 (m, 4H), 2.57 (m, 4H), 2.35 (s, 3H).

MS m/z 325 (M$^+$), 256, 81, 69 (100), 41.

Elemental analysis (C$_{18}$H$_{19}$N$_3$OS): compliant.

9-(4-Methylpiperazin-1-yl)pyrrolo[2,1-b][1,3]benzothiazepine-1,10-dicarbaldehyde (3) (ST2147)

A mixture of phosphorus oxychloride (18 μL, 30 mg, 0.198 mmol) and N-methylformanilide (24 μL, 26 mg, 0.198 mmol) was stirred for 30 minutes at room temperature. Then solid (1) (30 mg, 0.100 mmol) was added and the resulting mixture was stirred overnight at room temperature. Then water was added and the water phase was extracted with dichloromethane (3×2.5 mL). Combined organic layers were dried over sodium sulphate, filtered and evaporated. Purification was accomplished by means of flash chromatography (5% methanol in dichloromethane) and afforded 11.3 mg of the pure desired product as a yellowish crystalline solid (35% yield).

$^1$H NMR (CDCl$_3$) δ 9.68 (s, 1H), 9.42 (s, 1H), 7.59 (m, 2H), 7.42 (m, 2H), 6.87 (m, 1H), 6.31 (m, 1H), 3.70–3.62 (m, 4H), 2.59 (m, 4H), 2.38 (s, 3H).

MS m/z 353 (M$^+$), 324, 295, 83, 70 (100), 57, 43.

Elemental analysis (C$_{19}$H$_{19}$N$_3$O$_2$S): compliant.

1-Methyl-9-(4-methylpiperazin-1-yl)pyrrolo[2,1-b][1,3]benzothiazepine (4) (ST2092)

To a solution of (2) (0.035 g, 0.107 mmol) in absolute ethanol (0.70 mL), hydrazine monohydrate (182 μL, 0.019 g, 3.74 mmol) was added. The resulting mixture was stirred at reflux for 1 hour. After that time the solvent was removed under vacuum; the yellow solid obtained was dissolved in toluene (0.76 mL) and potassium tert-butoxyde (0.036 g, 0.321 mmol) was added. The reaction mixture was refluxing for further 8 hours. Then water was added, the organic phase was separated and the aqueous phase was extracted with dichloromethane; combined organic layers were dried over sodium sulphate, filtered and evaporated. The crude product obtained was chromatographed (20% methanol in ethylacetate). The desired pure product was obtained in a yield of 60%.

$^1$H NMR (CDCl$_3$) δ 7.62 (m, 1H), 7.48 (m, 1H), 7.26 (m, 2H), 6.32 (s, 1H), 6.03 (m, 1H), 5.90 (m, 1H), 2.89 (m, 4H), 2.53 (m, 4H), 2.34 (s, 3H), 2.20 (s, 3H).

MS m/z 311 (M$^+$), 256, 213, 98, 69, 55 (100).

Elemental analysis (C$_{18}$H$_{21}$N$_3$S): compliant.

1-Methylenoxime-9-(4-methylpiperazin-1-yl)pyrrolo[2,1-b][1,3]benzothiazepine (5) (ST2129)

To a solution of (2) (0.010 g, 0.031 mmol) in dichloromethane (1.00 mL), hydroxylamine hydrochloride (0.043 g, 0.062 mmol) and pyridine (5 μL, 0.049 g, 0.062 mmol) were added. The reaction mixture was stirred 1 hour at room temperature then dry potassium carbonate (0.008 g, 0.062 mmol) was added and the mixture was stirred for further 72 hours. After that time hydroxylamine hydrochloride (0.043 g, 0.062 mmol) and dry potassium carbonate (0.017 g, 0.124 mmol) were added and the solution was stirred at 25° C. overnight. Then water was added, the organic phase was separated and the aqueous phase was extracted with dichloromethane; combined organic layers were dried over sodium sulphate, filtered and evaporated. The crude product obtained was chromatographed (10% methanol in ethyl ether) to afford 2.5 mg of the desired product. (17% yield).

$^1$H NMR (CDCl$_3$) δ 7.80 (s, 1H);7.68 (m, 1H), 7.48 (m, 1H), 7.30 (m, 2H), 6.94 (s, 1H), 6.38 (d, 1H, J=3.9 Hz), 6.15 (d, 1H, J=3.8 Hz), 3.02 (m, 4H), 2.62 (m, 4H), 2.40 (s, 3H), 2.20 (s, 3H).

MS m/z 340 (M$^+$), 323, 297, 225, 99, 70 (100), 56, 43.

Elemental analysis (C$_{18}$H$_{21}$N$_4$OS): compliant.

1-Hydroxymethyl-9-(4-methylpiperazin-1-yl)pyrrolo[2,1-b][1,3]benzothiazepine (6) (ST2096)

To a solution of (2) (17 mg, 0.052 mmol) in absolute ethanol (2.36 mL), sodium borohydride (7.13 mg, 0.188 mmol) was added. The resulting mixture was stirred overnight at room temperature. After that time the solvent was removed, the residue was treated with water and the solution was extracted with dichloromethane; combined organic layers were dried over sodium sulphate, filtered and evaporated. The crude product obtained was chromatographed (10% methanol and 10% triethylamine in ethyl acetate) to afford 9.5 mg of the desired pure product (yield 58.8%).

$^1$H NMR (CDCl$_3$) δ 7.63 (m, 1H), 7.49 (m, 1H), 7.29 (m, 2H), 6.76 (s, 1H), 6.14 (d, 1H, J=3.7 Hz), 6.05 (d, 1H, J=3.8 Hz), 4.51 (m, 1H); 3.05 (m, 4H); 2.47 (m, 4H), 2.32 (s, 3H).

MS m/z 327 (M$^+$), 296, 225, 198, 87, 70 (100), 58.

Elemental analysis (C$_{18}$H$_{21}$N$_3$OS): compliant.

1-Isopropoxymethyl-9-(4-methylpiperazin-1-yl)pyrrolo[2,1-b][1,3]benzothiazepine (7) (ST2095)

To a solution of N-[9-(4-methylpiperazin-1-yl)pyrrolo[2,1-b][1,3]benzothiazepine-1-yl]-N-tosylhydrazyne (37 mg, 0.075 mmol) in 2-propanol (4.0 mL), sodium borohydride (13 mg, 0.449 mmol) was added in portions while stirring at 0° C. The resulting mixture was stirred for 24 hours at reflux then for 48 hours at room temperature. After that time the solvent was removed, the residue was treated with water and the solution was extracted with dichloromethane; combined organic layers were dried over sodium sulphate, filtered and evaporated to give the crude product which was chromatographed (0.8% methanol in ethyl acetate) to afford pure (7) as yellowish crystals (51.4% yield).

$^1$H NMR (CDCl$_3$) δ 7.63 (m, 1H), 7.48 (m, 1H), 7.27 (m, 2H), 6.76 (s, 1H), 6.14 (m, 1H), 6.05 (m, 1H), 4.37 (s, 1H); 3.60 (m, 1H), 2.52 (m, 4H), 2.92 (m, 4H), 2.34 (s, 3H), 1.17 (s, 3H), 1.14 (s, 3H).

MS m/z 369 (M$^+$) (100), 326, 310, 296, 97, 70.

Elemental analysis (C$_{21}$H$_{27}$N$_3$OS): compliant.

7-Chloro-9-(4-ethylpiperazin-1-yl)pyrrolo[2,1-b][1,3]benzothiazepine (8) (ST2148)

Starting from 7-chloro-9,10-dihydropyrrolo[2,1-b][1,3]benzothiazepin-9-one (0.19 g, 0.76 mmol) and N-ethylpiperazine (0.70 mL, 6.13 mmol), the title compound was obtained following the above described procedure for (1). After purification, 0.19 g of the desired product were obtained as a white solid (yield 74%).

$^1$H NMR (CDCl$_3$) δ 7.62 (d, 1H, J=1.9 Hz), 7.41 (d, 1H, J=8.0 Hz), 7.22 (d, 1H, J=8.0 Hz), 6.73 (m, 1H), 6.57 (s, 1H), 6.20 (m, 1H), 6.10 (m, 1H), 2.88 (m, 4H), 2.50 (m, 6H), 1.10 (t, 3H, J=7.1 Hz).

Elemental analysis (C$_{18}$H$_{20}$ClN$_3$S): compliant.

7-Chloro-9-(4-methylhexahydro-1H-1,4-diazepin-1-yl) pyrrolo[2,1-b]-[1,3]benzothiazepine (9) (ST2149)

The title compound was obtained following the above described procedure for (1), starting from 7-chloro-9,10-dihydropyrrolo[2,1-b][1,3]benzothiazepin-9-one (0.03 g, 0.12 mmol) and 1-methylhomopiperazine (0.06 mL, 5.41 mmol). After purification the desired product was obtained with a yield of 41%.

$^1$H NMR (CDCl$_3$) δ 7.53 (d, 1H, J=2.4 Hz), 7.43 (d, 1H, J=8.8 Hz), 7.22 (dd, 1H, J=8.4, 2.4 Hz), 6.75 (m, 1H), 6.55 (s, 1H), 6.19 (m, 1H), 6.11 (m, 1H), 3.20 (m, 4H), 3.15–2.61 (m, 4H), 2.40 (s, 3H), 1.95 (m, 2H).

MS m/z 345 (M$^+$) (100), 205, 140, 97.

Elemental analysis (C$_{18}$H$_{20}$ClN$_3$S): compliant.

7-Bromo-9-(4-methylpiperazin-1-yl)pyrrolo[2,1-b][1,3] benzothiazepine (10) (ST2093)

A solution of 7-bromo-9,10-dihydropyrro[2,1-b][1,3]benzothiazepin-9-one (0.10 g, 0.34 mmol), N-methylpiperazine (0.169 mL, 1.53 mmol) and trimethylsilyl triflate (0.169 mL, 0.935 mmol) was heated at 120° C. under stirring, after a few minutes further 0.50 mL of N-methylpiperazine were added and the reaction was kept for 3 hours at 120° C. After that time water was added and the water phase was extracted with dichloromethane. The organic layer was dried over sodium sulphate, filtered and evaporated to give the crude product that was purified by means of flash chromatography (20% methanol in ethyl acetate) to afford 0.114 g of the title compound as a yellowish solid (84% yield).

$^1$H NMR (CDCl$_3$) δ 7.76 (s, 1H),7.37 (m, 2H), 6.73 (m, 1H),6.57 (m, 1H), 6.20 (m, 1H), 6.10 (m, 1H), 2.87 (m, 4H), 2.53 (m, 4H), 2.35 (s, 3H); Elemental analysis (C$_{17}$H$_{18}$BrN$_3$S) C, H, N.

7-Bromo-9-(4-ethylpiperazin-1-yl)pyrrolo[2,1-b][1,3] benzothiazepine (11) (ST2150)

The title compound was obtained following the above described procedure for (10), starting from 7-bromo-9,10-dihydropyrrolo[2,1-b][1,3]benzothiazepin-9-one (0.10 g, 0.34 mmol), N-ethylpiperazine (0.169 mL, 1.53 mmol) and trimethylsilyl triflate (0.169 mL, 0.935 mmol); then further 0.50 mL of N-ethylpiperazine were added. After purification 0.125 g of the desired pure product was obtained as a white solid (94% yield).

$^1$H NMR (CDCl$_3$) δ 7.76 (s, 1H), 7.36 (s, 1H), 7.26 (s, 1H), 6.75 (m, 1H), 6.57 (s, 1H), 6.21 (m, 1H), 6.10 (m, 1H), 2.90 (m, 4H), 2.60–2.46 (m, 6H), 1.12 (t, 3H, J=7.0 Hz); MS m/z 390 (M$^+$+H), 356, 137, 111, 97, 84 (100), 69, 57.

Elemental analysis (C$_{18}$H$_{20}$BrN$_3$S): compliant.

7-fluoro-9-(4-methyl-1-piperazinyl)pyrrolo[2,1-b][1,3] benzothiazepine (ST1928)

The title compound was prepared starting from 7-fluoro-9,10-dihydropyrrolo[2,1-b][1,3]benzothiazepin-9-one and following the procedure A as described in example 1.

Molecular Pharmacology a) Evaluation of Ability to Interact with D$_1$, D$_2$, D$_3$ and 5HT$_{2a}$ Receptors.

Interaction with D$_1$, D$_2$, D$_3$, and 5HT$_{2a}$ receptors was studied using various different cerebral areas (striate D$_1$ and D$_2$; olfactory tubule D$_3$; prefrontal cortex 5HT$_{2a}$) according to the method described in the literature (Campiani et. al. *J. Med. Chem.* pp.3763–3772,1998).

Interaction with the D$_1$ receptor was evaluated using the radioligand [$^3$H]-SCH 23390 (0.4 μM) and the aspecific binding was determined in the presence of (−)-cis-flupentixol (10 μM). For the D$_2$ receptor $^3$H-spiperone (0.2 nM) was used and the aspecific binding was determined in the presence of 100 μM of (−) sulpyride.

As regards the D$_3$ receptor, the radioligand chosen was $^3$H-7-OH-DPAT which was used at the concentration of 0.2 μM and the aspecific binding was obtained in the presence of dopamine 1 μM. Lastly, interaction with 5HT$_{2a}$ was evaluated using $^3$H-ketanserine (0.7 μM) and the aspecific binding was determined in the presence of methysergide 1 μM.

b) Evaluation of Ability to Interact with the H$_1$ Histamine and α$_1$-Adrenergic Receptors.

Interaction with H$_1$ Receptors

Interaction with H$_1$ receptors was studied using rat cortex membranes incubated with [$^3$H]-pyrilamine at a concentration of 1 nM in phosphate buffer 50 mM pH 7.4 for 60 minutes at 30° C., according to the procedure described by Hill (S. J. Hill, P. C. Emson, J. M. Young "*J. Neurochemistry*" 31, 997–1004; 1978). Aspecific binding was determined in the presence of 100 μM of pyrilamine.

Interaction with α$_1$ Receptors

The interaction with β$_1$-adrenergic receptors was evaluated on rat cortex using the radioligand [$^3$H]-prazosin (0.2 nM), according to the procedure described by Greenglass (P. Greenglass, R. Bremner "*Eur. J. Pharmacol.*" 55, 323–326; 1979).

Aliquots of membrane protein were incubated for 30 minutes at 25° C. with the radioligand and the aspecific binding was determined in the presence of 100 μM of prazosin.

General Pharmacology

Evaluation of Catalepsy

The test was performed on Wistar male rats (N=7 animals); catalepsy was evaluated by means of a metal bar measuring 0.6 cm in diameter positioned at a distance of 10 cm from the work surface. The substance studied, in the form of maleic acid salt (ST1699), was administered subcutaneously 30 minutes prior to the evaluation. The subsequent evaluation times were 60, 90, 120, 180, 240, and 300 minutes after administration. The test consisted in positioning the animal with its forepaws on the bar and measuring the time the animal remained attached to the bar, considering an end-point of 60 seconds (N. A. Moore et al. *Journal of Pharmacology and Experimental Therapeutics* Vol. 262 pp. 545–551 (1992)).

Results and Discussion

Table 1 gives the means and standard deviation of the affinity values expressed as Ki (nM) of the study product ST1508 for the dopaminergic receptors D$_1$, D$_2$ and D$_3$; the serotoninergic receptor 5-HT$_{2a}$, the alpha$_1$-adrenergic receptor and the H$_1$ histaminergic receptor.

In addition, the table presents the affinity values for the above-mentioned types of receptors for the compound haloperidol, as a reference belonging to the neuroleptic drug class, for the purposes of verifying the typical antipsychotic profile of the product studied.

TABLE 1

|  | $D_1$ $K_i \pm ds$ | $D_2$ $K_i \pm ds$ | $D_3$ $K_i \pm ds$ | 5-$HT_{2a}$ $K_i \pm ds$ | $\alpha_1$ $K_i \pm ds$ | $H_1$ $K_i \pm ds$ |
|---|---|---|---|---|---|---|
| ST1508 | 1.9 ± 0.1 | 0.43 ± 0.04 | 2.0 ± 0.1 | 0.34 ± 0.05 | 4.3 ± 0.1 | 2.7 ± 0.02 |
| Haloperidol | 318 ± 59 | 4.81 ± 1.0 | 18.2 ± 1.5 | 164 ± 23.6 | 12 ± 2.5 | 386 ± 0.001 |

The product ST1508 shows a substantial ability to interact with the receptor types considered. In particular, it can be seen that the low affinity values for the $D_1$, $D_2$ and $D_3$ receptors indicate a strong reaction of the product with the dopaminergic system, which is even better than that found for the haloperidol receptor profile.

This particular receptor profile enables the compounds according to the invention described herein to be defined as classic antipsychotic agents. In fact, the $D_1$, $D_2$ and $D_3$ receptor affinity values indicate that the compounds are capable of exerting an effect on the hyperactivity condition of the mesolimbic dopaminergic system responsible for acute and chronic psychotic states.

Table 2 gives the means and standard deviation of the affinity values expressed as Ki (nM) of the preferred compounds ST1988, ST1928 and ST2092 for the dopaminergic receptors $D_1$, $D_2$ $D_3$; and for serotoninergic receptor 5-$HT_{2a}$. Typical (haloperidol) and a typical (Clozapine, Olanzapine) antipsychotics binding affinities are represented.

TABLE 2

| Compound | 5-$HT_{2a}$ Ki (nM) ± ds | $D_1$ Ki (nM) ± ds | $D_2$ Ki (nM) ± ds | $D_3$ Ki (nM) ± ds |
|---|---|---|---|---|
| Clozapine | 10 ± 1 | 353 ± 35 | 250 ± 57 | 319 ± 65 |
| Olanzapine | 4 ± 1 | 85 ± 3.5 | 69 ± 17 | 26 ± 7.75 |
| Haloperidol | 164 ± 24 | 318 ± 59 | 4.8 ± 1 | 18 ± 1.5 |
| ST1508 | 0.34 ± 0.05 | 1.9 ± 0.1 | 0.43 ± 0.04 | 2.0 ± 0.1 |
| ST1899 | 0.6 ± 0.1 | 19 ± 1.3 | 17 ± 4.5 | 8 ± 0.5 |
| ST1928 | 0.35 ± 0.04 | 7.7 ± 0.58 | 8.5 ± 5 | 2.70 ± 0.10 |
| ST2092 | 1.1 ± 0.05 | 154 ± 116 | 126 ± 15 | 18 ± 1 |

Preferred compounds display high affinity at 5-$HT_2$ receptor as a typical reference antipsychotics Clozapine and Olanzapine and differently from Haloperidol.

Moreover, ST1899, ST1928 and ST2092 binding affinity at 5 $HT_2$ receptor is greater than $D_2$ dopamine receptor, which resembles the binding characteristics of a typical antipsychotics.

In vitro, classification of a typical and typical antipsychotic drugs could be done considering 5-$HT_2$ versus $D_2$ affinity (pKi values) ratio and Log Y score (Meltzer H Y et al. "Classification of typical and atypical antipsychotics drugs on the basis of dopamine $D_1$, $D_2$ and serotonin$_2$ pKi values" J. Pharm. Exp. Ther. 1989, 251, 238–246). Antipsychotic with a 5-$HT_2$ versus $D_2$ affinity (pKi values) ratio greater than 1.12 and Log Y score smaller than 6.48 has an a typical profile. In table 3 the affinity ratios and Log Y score of typical (Haloperidol) and a typical antipsychotics (Clozapine and Olanzapine) are compared to those of preferred compounds. ST1899, ST1928, ST2092 display an a typical profile in similar fashion to Clozapine and Olanzapine. Furthermore, ST2092 display an a typical profile better than reference compounds.

About ST1508, 5-$HT_2$ versus $D_2$ affinity ratio and LogY score values confirm a typical profile for this compound. Despite of high capacity interaction at $5HT_2$ receptor (similarly to ST1928, ST1899, and ST2092), ST1508 has a more marked dopaminergic profile than that of its direct structural analogues ST1899 ST1928 and ST2092.

TABLE 3

| Compound | 5-$HT_{2a}$ pKi | $D_1$ pKi | $D_2$ pKi | $D_3$ pKi | 5-$HT_2/D_2$ Ratio pKi values | LogY |
|---|---|---|---|---|---|---|
| Clozapine | 8.00 | 6.45 | 6.60 | 6.50 | 1.21 | 3.89 |
| Olanzapine | 8.4 | 7.07 | 7.16 | 7.41 | 1.17 | 4.69 |
| Haloperidol | 6.78 | 318 | 8.32 | 7.74 | 0.82 | 9.14 |
| ST1508 | 9.47 | 8.72 | 9.37 | 8.70 | 1.01 | 8.20 |
| ST1899 | 9.19 | 7.71 | 7.76 | 8.08 | 1.18 | 4.98 |
| ST1928 | 9.46 | 8.11 | 8.07 | 8.57 | 1.17 | 5.36 |
| ST2092 | 8.95 | 6.81 | 6.9 | 7.74 | 1.30 | 3.19 |

These results render the compounds ST1899 ST1928 and ST2092 particularly useful in the treatment of positive and negative symptoms of schizophrenia.

Evaluation of Catalepsy

By means of the test used for evaluating catalepsy in the rat, ST1699 affinity for the $D_2$ receptor subtype of the nigrostriatal dopaminergic system was verified.

Table 4 gives the percentages of animals presenting catalepsy at the various different times after administration of subacute doses of the study compound.

TABLE 4

|  |  | Time (minutes) of catalepsy evaluation after Administration | | | | |
|---|---|---|---|---|---|---|
|  | mg/kg | 30 min | 60 min | 90 min | 120 min | 180 min |
| ST1699 | 0.6 | 33 | 66 | 83 | 100 | 100 |
|  | 0.3 | 0 | 0 | 17 | 17 | 33 |
|  | 0.15 | 0 | 0 | 0 | 0 | 0 |
| Haloperidol | 0.2 | 0 | 70 | 100 | 100 | 100 |

The product ST1699 induced the occurrence of catalepsy as a result of the highest dose among those used (0.6 mg/kg). The effects were comparable to those induced by 0.2 mg/kg of haloperidol.

The occurrence of catalepsy only as a result of the highest dose may indirectly verify the ability of the compound exemplified by ST1699 to interact with the 5-$HT_{2a}$ receptor. In fact, the antagonism to the above-mentioned receptor modulates the dopaminergic activity of the nigrostriatal system, thus limiting the possibility of the occurrence of catalepsy.

Thus, on the strength of these results and its substantial receptor affinity, the compound ST1508, alias ST1699, proves to be a classic antipsychotic agent in which the dose necessary to obtain an effective therapeutic response can be significantly reduced. Thanks to this potential, the prolonged use of this product, in chronic diseases such as schizophrenia, would be associated with a better tolerability.

What is claimed is:

1. A compound of formula (I):

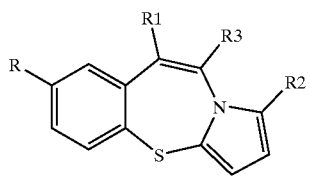

where:
- R=H, Cl, Br, F, I, $C_1$–$C_4$ alkoxy, $C_1$–$C_4$ alkylthio, $C_1$–$C_4$ alkyl, or $C_5$–$C_6$ cycloalkyl;
- $R_1$=$C_1$–$C_4$ dialkylamine, where the alkyl groups are the same or different from one another, 4-alkyl-1-piperazinyl, 4-hydroxyalkyl-1-piperazinyl, 1-imidazolyl, 4-alkyl-1-piperidinyl, or 4-alkyl-1-homopiperazinyl;
- $R_2$=H, $C_1$–$C_4$ alkoxy, $C_1$–$C_4$ alkylthio, $C_1$–$C_4$ alkyl, CHO or CH=NOH;
- $R_3$=H, CHO; or the pharmaceutically acceptable salts thereof.

2. The compound according to claim 1, wherein $R_1$ is 4-alkyl-1-piperazinyl.

3. The compound according to claim 1, wherein R is H, Cl, Br, F or I.

4. The compound according to claim 1, which is 7-chloro-9-(4-methylpiperazin-1-yl)pyrrolo [2,1-b][1,3] benzothiazepine or a pharmaceutically acceptable salt thereof.

5. The compound according to claim 4, where the pharmaceutically acceptable salt is maleate.

6. The compound according to claim 1, where R=H or F; $R_2$ _H, CHO, or $CH_3$; and $R_3$ _H; and $R_1$ _4-methyl-1-piperazinyl.

7. The compound according to claim 6, selected from the group consisting of:
- -9-(4-methyl-1-piperazinyl)pyrrolo[2,1-b][1,3] benzothiazepine;
- -7-fluoro-9-(4-methyl-1-piperazinyl)pyrrolo[2,1-b][1,3] benzothiazepine; and
- -1-methyl-9-(4-methylpiperazin-1-yl)pyrrolo[2,1-b][1,3] benzothiazepine.

8. A pharmaceutical composition comprising as an active ingredient a compound of claim 1 in a mixture with at least one pharmaceutically acceptable vehicle and/or excipient.

9. A method of treating antipsychotic activity comprising administering to a subject a compound according to claim 1.

10. A method of treating classic antipsychotic activity comprising administering to a subject a compound according to claim 4.

11. A method of treating a typical antipsychotic activity comprising administering to a subject a compound according to claim 6.

12. A method for the treatment of schizophrenia comprising administering to a subject a compound according to claim 1.

13. A method for the treatment of a disorder related to increased activity of the mesolimbic dopaminergic pathway and/or mesocortical dopaminergic hypofunction comprising administering to a subject a compound of claim 6.

14. The method of claim 13 wherein the disorder is a paranoid state, manic-depressive state, affective disorder, social withdrawal, personality regression, hallucinations or cognitive dysfunction.

* * * * *

UNITED STATES PATENT AND TRADEMARK OFFICE
CERTIFICATE OF CORRECTION

PATENT NO. : 6,710,041 B2
DATED : March 23, 2004
INVENTOR(S) : Minetti et al.

It is certified that error appears in the above-identified patent and that said Letters Patent is hereby corrected as shown below:

Title page,
Item [30], Foreign Application Priority Data, should read as follows:
-- [30]   Foreign Application Priority Data
August 1, 2000 (IT) ................................. RM 2000 A000432 --

Signed and Sealed this

Twenty-second Day of June, 2004

JON W. DUDAS
*Acting Director of the United States Patent and Trademark Office*